United States Patent
Xu et al.

(10) Patent No.: US 12,054,502 B2
(45) Date of Patent: Aug. 6, 2024

(54) MULTIFUNCTIONAL IMMUNITY-TARGETED MICROMOLECULE ANTI-CANCER MEDICINE BESTAZOMIB (BESTAZOMIB) AND PREPARATION METHOD AND APPLICATION THEREOF

(71) Applicant: SHANDONG HUBBLE KISEN BIOLOGICAL TECHNOLOGY CO., LTD., Shandong (CN)

(72) Inventors: Wenfang Xu, Shandong (CN); Jian Zhang, Shandong (CN); Yuqi Jiang, Shandong (CN); Xiaobo Xu, Shandong (CN); Xiaoyang Li, Shandong (CN); Leqiao Tan, Shandong (CN); Yongxue Huang, Shandong (CN); Xuejian Wang, Shandong (CN); Zhen Zhang, Shandong (CN)

(73) Assignee: SHANDONG HUBBLE KISEN BIOLOGICAL TECHNONLOGY CO., LTD., Shandong (CN)

( * ) Notice: Subject to any disclaimer, the term of this patent is extended or adjusted under 35 U.S.C. 154(b) by 738 days.

(21) Appl. No.: 17/267,183

(22) PCT Filed: Aug. 5, 2019

(86) PCT No.: PCT/CN2019/099305
§ 371 (c)(1),
(2) Date: Feb. 9, 2021

(87) PCT Pub. No.: WO2020/029925
PCT Pub. Date: Feb. 13, 2020

(65) Prior Publication Data
US 2021/0300949 A1     Sep. 30, 2021

(30) Foreign Application Priority Data

Aug. 9, 2018   (CN) .................. 201810902222.0

(51) Int. Cl.
    *C07F 5/02*    (2006.01)
    *A61P 35/02*   (2006.01)
    *A61P 35/00*   (2006.01)

(52) U.S. Cl.
    CPC .............. *C07F 5/025* (2013.01); *A61P 35/02* (2018.01)

(58) Field of Classification Search
    CPC .......... C07F 5/025; A61P 35/02; A61P 35/00; Y02P 20/55
    See application file for complete search history.

(56) References Cited

U.S. PATENT DOCUMENTS

2015/0051172 A1*   2/2015   Vaya ................... A61K 31/194
                                                           514/64

FOREIGN PATENT DOCUMENTS

CN   105646273 A   6/2016
CN   106478701 A   3/2017
(Continued)

*Primary Examiner* — Jeffrey S Lundgren
*Assistant Examiner* — Alexander K. Showalter
(74) *Attorney, Agent, or Firm* — NKL Law; Bin Lu

(57) ABSTRACT

A multifunctional immunity-targeted micromolecule anti-cancer medicine Citrate Bestazomib and preparation method and application thereof. The structure of the multifunctional immunity-targeted micromolecule anti-cancer medicine Bestazomib Citrate is shown as follows:

(Continued)

The multifunctional immunity-targeted micromolecule anticancer medicine Citrate Bestazomib has an activity-inhibiting effect on APN/CD13, also has an activity-inhibiting effect on tumor proteasome, and can be applied to the development of medicines for treating malignant tumors.

11 Claims, 7 Drawing Sheets

(56) References Cited

FOREIGN PATENT DOCUMENTS

| | | |
|---|---|---|
| CN | 106916177 A | 7/2017 |
| CN | 109053782 A | 12/2018 |
| WO | 2018133661 A1 | 7/2018 |

* cited by examiner

MULTIFUNCTIONAL IMMUNITY-TARGETED MICROMOLECULE ANTI-CANCER MEDICINE BESTAZOMIB (BESTAZOMIB) AND PREPARATION METHOD AND APPLICATION THEREOF

TECHNICAL FIELD

The invention relates to the technical field of medicinal chemistry, in particular to a multifunctional immunity-targeted micromolecule anti-cancer medicine Bestazomib Citrate (Bestazomib) and preparation method and application thereof.

BACKGROUND

Aminopeptidase N (APN/CD13) is a type II transmembrane zinc ion-dependent metalloprotease, belonging to the Gluzincins subfamily of the M1 family, which binds to the cell membrane as a homodimer glycoprotein (*Nucleic Acids Res.*, 1999, 27(1): 325-331). APN is expressed on the cell surface of various tissues, such as central nervous system synaptic cells, synovial fluid fibroblasts, activated endothelial cells, hepatocytes, intestinal mucosal epithelial cells, placenta, bone marrow progenitor cells, monocytes, Osteoclasts, etc., especially enriched in brush border cells of the kidney and intestine (*Haema.*, 2003, 4(6):453-461). In addition, compared with normal cells, APN is expressed at high levels on the surface of a variety of tumor cells such as multiple myeloma, liver cancer, melanoma, ovarian cancer, prostate cancer, colon cancer, pancreatic cancer, breast cancer, and lung cancer.

In recent years, a large number of experimental studies in many laboratories around the world have proved that aminopeptidase N (APN/CD13) is a surface biomarker of human liver cancer stem cells, which is closely related to the chemotherapy resistance, recurrence and metastasis of liver cancer (*J Clin Invest* 2010, 120, 3326-3339); APN/CD13 has been shown to mediate neovascularization in the tumor microenvironment (*PNAS* 2007,104(11):4588-4593; 2012, 109(5):1637-1642). APN/CD13 plays an important role in the tumor microenvironment. It accelerates the growth of tumors by influencing the level of certain cytokines in the tumor tissue microenvironment, promotes the formation of microvessels in tumor tissues, and prevents the production of reactive oxygen free radicals (ROS) in cancer cells of tumor tissues caused by radiotherapy and chemotherapy, which leads to chemotherapy resistance, and then leads to the loss of immune function.

Ubenimex (Bestatin) is a dipeptide compound isolated from the culture of Streptomyces olivoreticuli. Ubenimex was marketed in Japan in 1987 as an immune enhancer for the treatment of leukemia; and it was listed in the domestic market in 1998 under the trade name Bestatin. Bestatin has obvious immunomodulatory function and significant anti-tumor activity. Bestatin's impact on the immune system is mainly reflected in its ability to effectively enhance the function of T and B lymphocytes, and at the same time increase the killing activity of natural killer cells (NK). In addition, it can also stimulate the regeneration and differentiation of bone marrow cells by promoting the synthesis of colony stimulating factors to achieve the effects of regulating, enhancing, exciting and restoring the body's immune function. Bestatin can inhibit the invasion of mouse melanoma highly metastatic strain B16BL6; it can also inhibit the formation of tube-like structures of HUVECs (*Cancer letter*, 2004,216(1):35-42). In the experiments of transplanted tumors in mice, it was found that Bestatin can inhibit tumor cell metastasis and tumor-induced angiogenesis (Bio. Pharm, Bull., 1996, 19(1): 6-10). Bestatin, as a small molecule immunopotentiator, has proven to be safe and effective in clinically adjuvant treatment of various cancers such as leukemia, multiple myeloma, myelodysplastic syndrome and other solid tumors with traditional chemotherapy drugs. However, single-drug administration has little effect (*Science*, 2000).

Bortezomib (MG-341) is a proteasome inhibitor developed by Millennium Corporation in the United States. It was approved for marketing by the FDA in 2003 and clinically used to treat multiple myeloma and relapsed and refractory mantle cell lymphoma. Bortezomib has obvious proliferation inhibitory effects on a variety of malignant tumor cells in vitro, and has obvious anti-tumor effects in a series of hematological malignancies and solid tumors such as small cell lung cancer, prostate cancer and pancreatic cancer. However, due to low oral bioavailability and stability, bortezomib can only be administered by injection.

Ixazomib Citrate (MLN9708), developed by Takeda Pharmaceutical Company, is an oral, highly selective proteasome inhibitor. It was first approved for marketing in the United States on Nov. 20, 2015. It is used to treat multiple myeloma that has received at least first-line treatment in the past. Compared with the listed proteasome inhibitors, Ixazomib has the following advantages: Ixazomib is still effective for patients with multiple myeloma resistant to first-generation inhibitors such as bortezomib; Ixazomib is an oral proteasome inhibitor and only needs to be taken every week once; compared with bortezomib, Ixazomib has lower peripheral neurotoxicity.

Since the functions and targets of the existing malignant tumor treatment drugs are relatively single, the chemotherapy of malignant tumors generally requires multi-drug combination therapy, especially the use of traditional cytotoxic chemotherapeutics and biological immune adjuvants or targets that inhibit the growth of new blood vessels. The combination of kinase inhibitor drugs has become the preferred option for tumor clinical chemotherapy. However, in the process of combination medication, cancer patients need to receive multiple and large amounts of drug treatment, making them more likely to face the dangers caused by drug interactions, and also increasing the cost of treatment. Therefore, the design and development of multifunctional anti-cancer drugs has become a research hotspot in the field of new drug design in medicinal chemistry in recent years.

SUMMARY OF THE INVENTION

In view of the above-mentioned shortcomings of the prior art, the purpose of the present invention is to provide a multifunctional targeted immune small molecule anticancer drug Bestazomib Citrate. It has inhibitory activity on APN/CD13, as well as tumor proteasome.

In order to achieve the above objectives, the present invention adopts the following technical solutions:

In the first aspect of the present invention, there is provided a compound represented by Formula I, or an optical isomer, a diastereomer, a racemate or the mixture of the three, or a pharmaceutically acceptable salt thereof, or a solvate thereof;

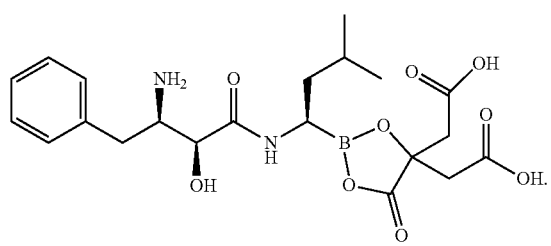 [SMILES: CC(C)C[C@H](NC(=O)[C@@H](O)[C@H](N)Cc1ccccc1)B1OC(=O)C(CC(=O)O)(CC(=O)O)O1]

In the second aspect of the present invention, there is provided an intermediate for preparing the compound of Formula I, the structure of which is as shown in Formula II:

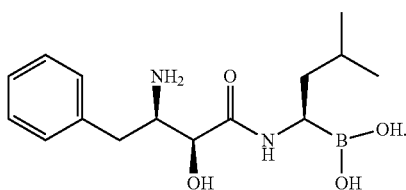

In the third aspect of the present invention, there is provided a method for preparing the compound represented by Formula I, comprising the following steps:

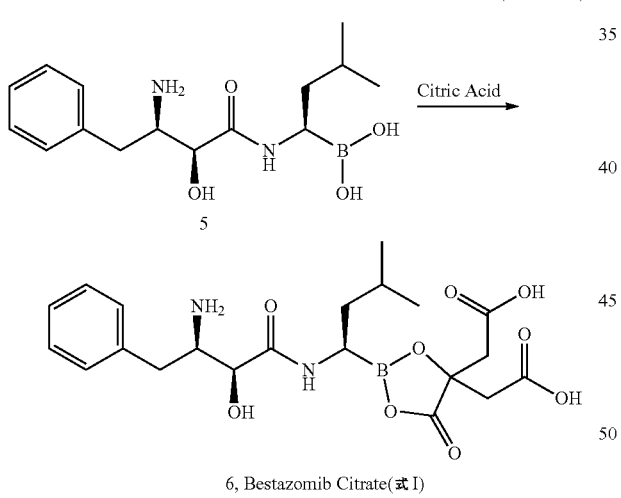

reacting intermediate 5 with citric acid to obtain the compound represented by Formula I. In another preferred embodiment, the method comprises the following steps:

using (2S,3R)-3-amino-2-hydroxy-4-phenylbutyric acid (AHPA) as the raw material, the primary amino group was protected by Cbz to obtain intermediate 2; reacting intermediate 2 with (R)-1-amino-3-methylbutylboronic acid pinanediol ester trifluoroacetate in anhydrous DCM catalyzed by EDCI and HOBt to obtain intermediate 3; deprotecting the protective group of intermediate 3 by isobutylboronic acid to obtain intermediate 4; deprotecting Cbz of intermediate 4 under Pd/C and hydrogen to generate intermediate 5, and finally reacting intermediate 5 with citric acid to obtain compound of Formula I.

The synthetic route is as follows:

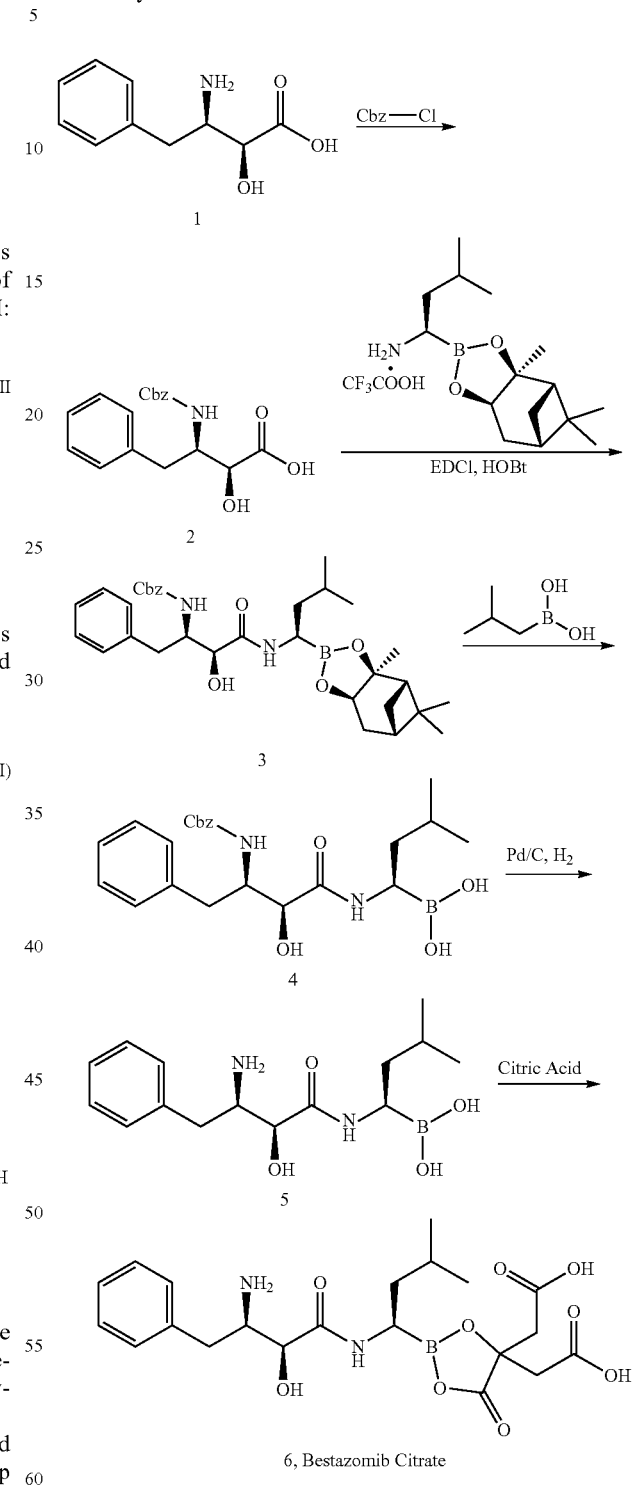

wherein, Cbz-Cl is benzyloxycarbonyl chloride, DCM is dichloromethane, EDCI is 1-(3-dimethylaminopropyl)-3-ethylcarbodiimide hydrochloride, HOBt is 1-hydroxybenzotriazole, Pd/C is palladium on carbon.

In the third aspect of the present invention, there is provided a use of the compound represented by the above Formula I, or the optical isomer, the diastereomer, the racemate or the mixture of the three, or the pharmaceutically acceptable salt thereof, or the solvate in the preparation of a multifunctional targeting inhibitor; preferably, the multifunctional targeting inhibitor has inhibitory activity on both aminopeptidase N and proteasome.

In the fourth aspect of the present invention, there is provided a use of the compound represented by the above Formula I, or the optical isomer, the diastereomer, the racemate or the mixture of the three, or the pharmaceutically acceptable salt thereof, or the solvate thereof in the preparation of medication for preventing or treating tumors.

Preferably, the tumors comprise: myeloma, leukemia and solid tumor.

In the fifth aspect of the present invention, there is provided a pharmaceutical composition, the active ingredient of which is the compound represented by Formula I, or the optical isomer, the diastereomer, the racemate or the mixture of the three, or the pharmaceutically acceptable salt thereof, or the solvate thereof.

Further, the pharmaceutical composition also comprises one or more pharmaceutically acceptable carriers or excipients.

Preferably, the pharmaceutical composition is an oral preparation or an injection preparation.

The application of the above-mentioned pharmaceutical composition in the preparation of pharmaceutical preparations for treating tumor diseases is also the protection scope of the present invention. Preferably, the tumor diseases comprise: myeloma, leukemia and solid tumor.

In the sixth aspect of the present invention, there is provided a method for treating tumor diseases, comprising administering a therapeutically effective amount of a compound represented by Formula I or a pharmaceutically acceptable salt thereof to a subject who is at risk of tumor disease or has been diagnosed with tumor disease.

The term "therapeutically effective amount" as used herein refers to the amount of the therapeutic agent required to treat, ameliorate the targeted disease or condition, or exhibit a detectable therapeutic effect.

The compound of the present invention is effective in a relatively wide dosage range. The actual dosage of the compound represented by Formula I of the present invention can be determined by the doctor according to the relevant situation. These conditions include: the subject's physical state, route of administration, age, weight, individual response to the drug, and the severity of symptoms, etc.

In the course of treatment, the above-mentioned compound of Formula I or a pharmaceutically acceptable salt thereof can also be used in combination with at least one other drug. The atomic composition or structures of the other drugs covered are all different from those of the compound of Formula I.

The beneficial effects of the present invention:
(1) The multifunctional targeted immune small molecule anticancer drug Bestazomib citrate of the present invention not only has inhibitory activity on APN/CD13, but also has inhibitory activity on tumor proteasome, and can be used for the development of therapeutic drugs for malignant tumors.
(2) The anti-cancer drug developed with Bestazomib citrate of the present invention as an active ingredient has multi-targets and multi-functionality. It can treat malignant tumors without being combined with other anti-tumor drugs, avoiding the risk caused by drug interactions in the process of combination drugs, and reducing the cost of treatment.

MODE OF CARRYING OUT THE INVENTION

Figure 1:
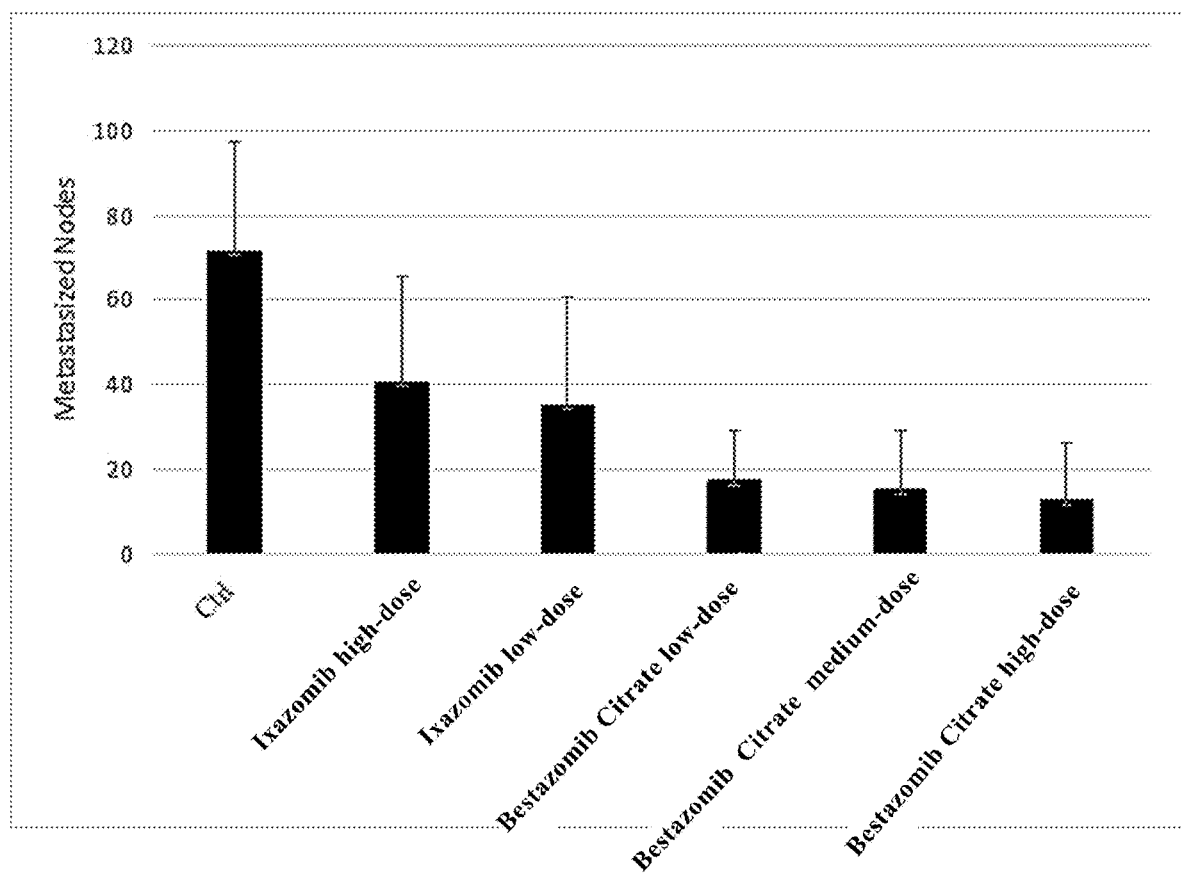
FIG. 1 shows the number of lung nodules in each group.

It should be pointed out that the following detailed descriptions are all illustrative and are intended to provide further explanations for the application. Unless otherwise indicated, all technical and scientific terms used herein have the same meaning as commonly understood by those of ordinary skill in the technical field to which this application belongs.

The terms and definitions used in this article have the following meanings:

"A pharmaceutically acceptable salt" refers to the salt form of the compound of Formula I which is therapeutically effective and non-toxic. It can be a cationic salt formed from any basic group (such as amino). Many such salts are known in the art, which are anionic salts formed on any basic group such as an amino group. Many of these salts are known in the art. Anionic salts can also be conveniently obtained by treating the basic form (I) with the corresponding acid, such acids include inorganic acids such as hydrochloric acid, sulfuric acid, nitric acid, phosphoric acid, etc.; or organic acids such as acetic acid, trifluoroacetic acid, propionic acid, glycolic acid, 2-hydroxypropionic acid, 2-oxopropionic acid, oxalic acid, malonic acid, succinic acid, maleic acid, fumaric acid, malic acid, tartaric acid, 2-hydroxy-1,2,3-tricarballylic acid, methanesulfonic acid, ethanesulfonic acid, benzene methanesulfonic acid, 4-methylbenzenesulfonic acid, cyclohexylsulfinic acid, 2-hydroxybenzoic acid, 4-amino-2-hydroxybenzoic acid, etc. These salts are well known to the skilled in the art, and the skilled in the art can prepare any salt provided by knowledge in the art. In addition, the skilled artisan can choose one salt instead of another based on factors such as solubility, stability, and ease of formulation. The determination and optimization of these salts are within the experience of skilled technicians.

As described in the background art section, the existing anti-tumor drugs have relatively single function and target, and usually require combination administration. However, combination administration will increase the risk caused by drug interactions and increase the cost of treatment. Based on this, the present invention provides a multifunctional targeted immune small molecule anticancer drug Bestazomib citrate.

The multifunctional targeted immune small molecule anticancer drug Bestazomib citrate of the present invention has the following structure:

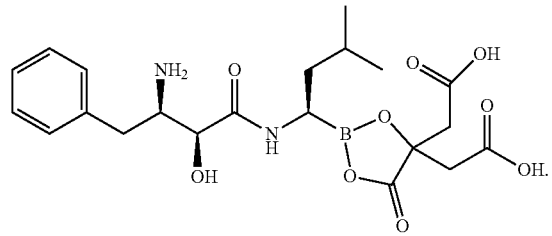

I

The chemical name of Bestazomib citrate is 2,2'-(2-((R)-1-((2S,3R)-3-amino-2-hydroxy-4-phenylbutanoylamino)-3-methyl butyl)-5-oxo-1,3,2-dioxaborolan-4,4-diyl) diacetic acid.

The design concept of the multifunctional targeted immune small molecule anticancer drug Bestazomib citrate of the present invention is: the present invention is based on the structure of Bestatin, the present invention first modifies the free carboxyl group in the molecular structure of Bestatin, and finds that it can still maintain its inhibitory activity on APN/CD13, but its activity in inhibiting tumor cell proliferation in vitro has not been increased, and it has no inhibitory activity on tumor proteasomes. In order to achieve the multi-targeting and multifunctionality of the compound, the present invention innovatively replaces the carboxyl group in the molecular structure of Bestatin with boric acid, and as a result, it is found that its inhibitory activity on tumor cell proliferation is significantly improved. However, the carboxyl part of the molecular structure of Bestatin is replaced with boric acid, and boric acid is easy to form a trimer structure, and its stability is poor, making it difficult to develop an oral anticancer drug. In order to further solve the problem of its stability, the present invention stabilizes boric acid by introducing citric acid into the molecular structure of the compound to enhance the stability of the compound. Through the above design process, the present invention designs and obtains the compound Bestazomib Citrate represented by Formula I. This compound is a prodrug molecule that further exerts cytoxicity by removing the citric acid moiety through metabolism in vivo.

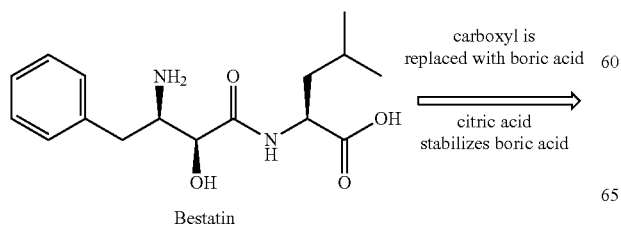

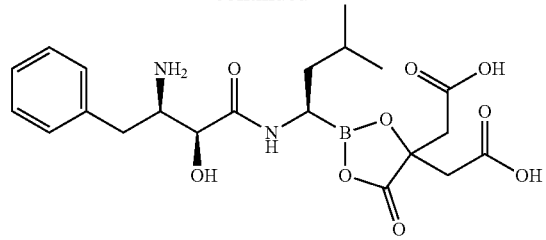

Bestazomib Citrate

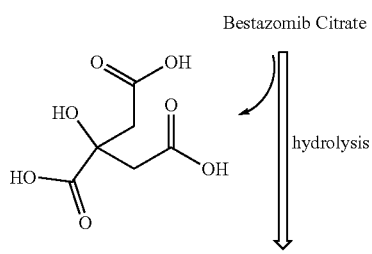

hydrolysis

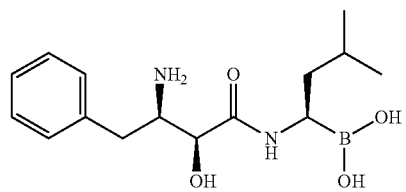

Bestazomib

Compared with the lead compound, the compound Bestazomib Citrate designed by the present invention has multi-targeting and multifunctionality. It not only has excellent inhibitory activity on APN/CD13, but also has better inhibitory activity on tumor proteasome. Cell experiments show that the compound Bestazomib Citrate of the present invention also has obvious inhibitory activity on the proliferation of various tumor cells.

Compared with the lead compound, the compound Bestazomib Citrate designed in the present invention has also great improvement in terms of pharmacokinetics, bioavailability, safety, and physical and chemical properties. It has good activity, many functions and good stability, and is very suitable for developing into multi-functional targeted immune small molecule anticancer drugs.

The multifunctional targeted immune small molecule anticancer drug Bestazomib citrate of the present invention is prepared by the following method:

using optically pure (2S,3R)-3-amino-2-hydroxy-4-phenylbutyric acid (AHPA) as raw material, the primary amino group was protected by Cbz to obtain intermediate 2. It was reacted with (R)-1-amino-3-methylbutyl borate pinanediol trifluoroacetate in anhydrous DCM catalyzed by EDCI and HOBt to obtain 3. Deprotecting the protective group of intermediate 3 by isobutylboronic acid to obtain key intermediate 4. Deprotecting Cbz of intermediate 4 under Pd/C and hydrogen to produce intermediate 5, and finally reacting with citric acid to obtain compound 6 (Bestazomib Citrate) represented by Formula I. The reaction formula is as follows:

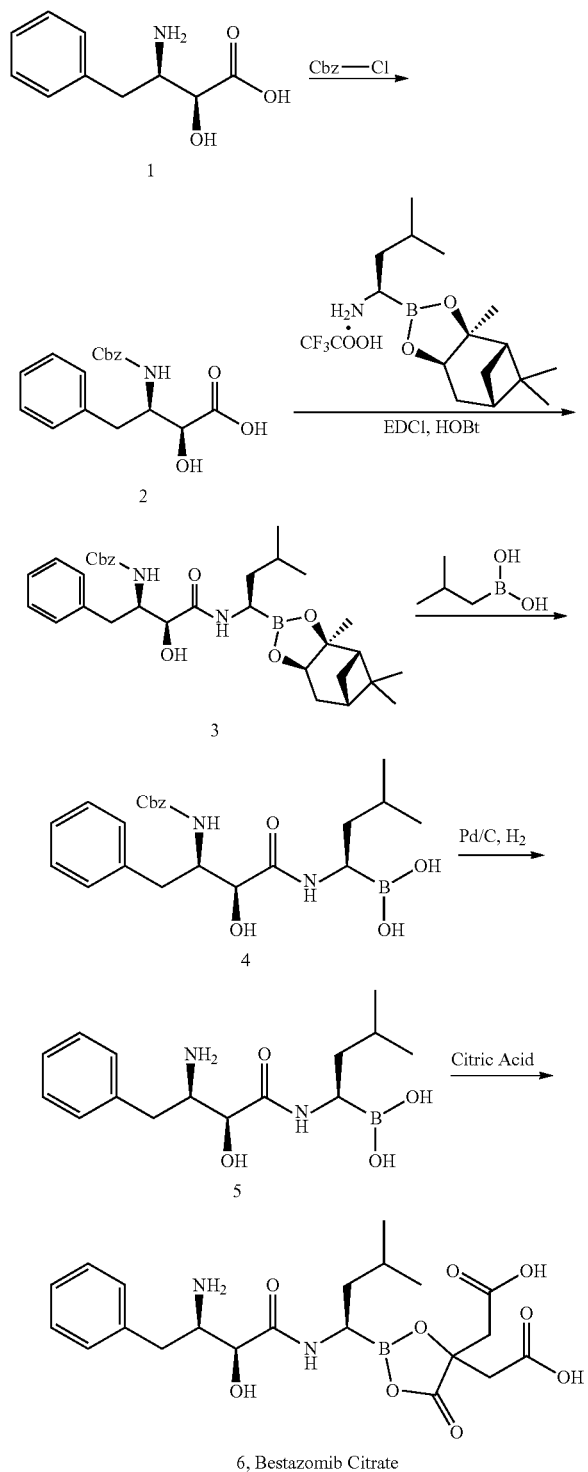

6, Bestazomib Citrate

Those skilled in the art can modify the above steps to improve the yield. They can determine the synthesis route based on the basic knowledge in the field, such as selecting reactants, solvents and temperature, and can avoid side reactions by using various conventional protecting groups, thus increasing yield. These conventional protection methods can be found in, for example, T.Greene, Protecting Groups in Organic Synthesis.

Pharmaceutical composition containing the compound of the present invention

Part of the derivatives of the present invention may exist in free form or in salt form. Those skilled in the art know many types of pharmaceutically acceptable salts of compounds and their preparation methods. Pharmaceutically acceptable salt includes conventional non-toxic salt, including quaternary ammonium salt formed by base of such compound with inorganic or organic acid.

The compound of the present invention can form hydrate or solvate. A person skilled in the art knows a method for forming a hydrate formed when a compound is lyophilized with water or a solvate formed when a solution is concentrated with a suitable organic solvent.

The present invention includes a pharmaceutical composition containing a therapeutic amount of a compound of the present invention, and one or more pharmaceutically acceptable carriers and/or excipients. Carriers include, for example, saline, buffered saline, glucose, water, glycerol, ethanol, and combinations thereof, as discussed in more detail below. If necessary, the composition may also contain a smaller amount of wetting or emulsifying agent, or pH buffering agent. The composition can be a liquid, suspension, emulsion, tablet, pill, capsule, extended-release preparation or powder. The composition can be formulated as a suppository with traditional binders and carriers such as triglycerides. Oral preparation may include standard carrier such as pharmaceutical grades of mannitol, lactose, starch, magnesium stearate, sodium saccharin, cellulose, magnesium carbonate, and the like. Depending on the preparation required, the preparation can be designed to mix, granulate and compress or dissolve the ingredients. In another approach, the composition can be formulated into nanoparticle.

The drug carrier used can be solid or liquid.

Typical solid carrier includes lactose, gypsum powder, sucrose, talc, gelatin, agar, pectin, acacia, magnesium stearate, stearic acid and the like. A solid carrier may include one or more substances that may simultaneously act as flavoring agent, lubricant, solubilizer, suspending agent, filler, glidant, compression aid, binder or tablet-disintegrating agent; it also can be an encapsulating material. In powder, the carrier is a finely divided solid, which is a mixture of finely divided active ingredients. In the tablet, the active ingredient is mixed with a carrier having the necessary compression properties in a suitable ratio and compressed in the desired shape and size. The powders and tablets preferably contain up to 99% active ingredient. Suitable solid carrier includes, for example, calcium phosphate, magnesium stearate, talc, sugar, lactose, dextrin, starch, gelatin, cellulose, methyl cellulose, sodium carboxymethyl cellulose, polyvinylpyrrolidone, low melting wax and ion exchange resin.

Typical liquid carrier include syrup, peanut oil, olive oil, water and the like. Liquid carrier is used to prepare solution, suspension, emulsion, syrup, tincture and sealed composition. The active ingredient can be dissolved or suspended in a pharmaceutically acceptable liquid carrier such as water, an organic solvent, a mixture of the two, or a pharmaceutically acceptable oils or fats. The liquid carrier may contain other suitable pharmaceutical additive such as solubilizer, emulsifier, buffer, preservative, sweeteners, flavoring agent, suspending agent, thickening agent, pigment, viscosity regulator, stabilizer or osmotic pressure-regulating agent. Suitable examples of liquid carrier for oral and parenteral administration include water (partially containing additives as described above, such as cellulose derivatives, preferably carboxymethylcellulose sodium salt solution), alcohols (including monohydric and polyhydric alcohols, such as ethylene glycol) and their derivatives, and oils (such as fractionated coconut oil and peanut oil). The carriers for parenteral administration can also be fats such as ethyl oleate and isopropyl myristate. The sterile liquid carrier is a sterile liquid composition for parenteral administration. The liquid carrier used in the pressurized composition may be halogenated hydrocarbon or other pharmaceutically acceptable propellant. The liquid pharmaceutical composition of a sterile solution or suspension solution can be used, for example, for intravenous, intramuscular, intraperitoneal or subcutaneous injection. Infusion can be single push or gradually injected, for example, 30 minutes of intravenous infusion. The compound can also be administered orally in the form of a liquid or solid composition.

The carrier or excipient may include time delay materials known in the art, such as glyceryl monostearate or glyceryl distearate, and may also include wax, ethyl cellulose, hydroxypropyl methyl cellulose, and methyl methacrylate and the like. When the formulation is used for oral administration, it is recognized that 0.01% Tween 80 in PHOS-ALPG-50 (phospholipid and 1,2-propanediol concentrated, A. Nattermann & Cie. GmbH) is used for the preparation of acceptable oral formulations of other compounds, which can be adapted to the formulation of various compounds of the present invention.

A wide variety of pharmaceutical forms can be used when administering the compounds of the present invention. If a solid carrier is used, the formulation can be in the form of tablets, powders or pellets placed in hard capsules or in the form of lozenges or trochiscus. The amount of solid carrier varies to a large extent, but is preferably from about 25 mg to about 1.0 g. If a liquid carrier is used, the formulation can be a syrup, emulsion, soft capsule, sterile injection solution or suspension in an ampoule or vial or a non-aqueous liquid suspension.

In order to obtain a stable water-soluble dosage form, the compound or a pharmaceutically acceptable salt thereof can be dissolved in an aqueous organic or inorganic acid, 0.3M succinic acid or citric acid solution. Alternatively, the acidic derivative can be dissolved in a suitable alkaline solution. If a soluble form is not available, the compound can be dissolved in a suitable co-solvent or combination thereof. Examples of such suitable co-solvents include, but are not limited to, ethanol, propylene glycol, polyethylene glycol 300, polysorbate 80, glycerol, polyoxyethylene fatty acid ester, fatty alcohol or glycerol hydroxy fatty acid ester, etc, in concentrations ranging from 0-60% of the total volume.

Various delivery systems are known and can be used for the administration of compounds or various other formulations including tablet, capsule, injectable solution, capsule in liposome, microparticle, microcapsule, and the like. Methods of introduction include, but are not limited to, cutaneous, intradermal, intramuscular, intraperitoneal, intravenous, subcutaneous, intranasal, pulmonary, epidural, ocular, and (usually preferred) oral routes. The compound may be administered by any convenient or other appropriate route, such as by injection or bolus injection, absorption through epithelial or mucosal routes (for example, oral mucosa, rectal and intestinal mucosa, etc.) or through drug-loaded stents and can be administered with other biologically active agents. It can be administered systemically or locally.

In order to enable those skilled in the art to understand the technical solutions of the present application more clearly, the technical solutions of the present application will be described in detail below in conjunction with specific examples.

The unspecified experimental materials used in the examples of the present invention are all conventional experimental materials in the field, and can be purchased through commercial channels.

Example 1: (2S, 3R)-3-((benzyloxycarbonyl) amino)-2-hydroxy-4-phenylbutyric acid (2)

AHPA (1, 1.95 g, 10.0 mmol) was dissolved in a mixed solution of 100 mL of tetrahydrofuran and 1 mol/L sodium hydroxide, and benzyloxycarbonyl chloride (1.88 g, 11.0 mmol) was added dropwise under ice bath conditions. After reacting at room temperature for 6 hours, the tetrahydrofuran in the reaction solution was evaporated, the aqueous phase was adjusted to pH=1 with 1 mol/L hydrochloric acid, extracted three times with ethyl acetate, the organic phases were combined, dried over anhydrous magnesium sulfate, and the solvent was evaporated to obtain a white solid 2 (2.11 g, 64%).

Example 2: (R)-1-((2S,3R)-3-((benzyloxycarbonyl) amino)-2-hydroxy-4-phenylbu tyramide)-3-methyl-butyl borate pinanediol ester (3)

Compound 2 (3.29 g, 10.0 mmol) was dissolved in 50 mL of anhydrous DCM, HOBt (1.49 g, 11 mmol) and EDCI (2.10 g, 11.0 mmol) were added under ice bath conditions, after 0.5 h, (R)-1-amino-3-methylbutyl borate pinanediol ester trifluoroacetate (4.07 g, 11.0 mmol), and triethylamine 1.5 mL were added. Removed the ice bath and reacted at room temperature for 5 h. After the reaction was completed, the organic layer was washed with water, 1M citric acid, saturated sodium bicarbonate, and saturated sodium chloride, respectively. Drying with anhydrous magnesium sulfate, filtering, and evaporating the solvent to obtain white solid 3 (3.05 g, 53%). $^1$H-NMR (400 MHz DMSO-$d_6$): 0.82 (s, 3H), 0.88-0.90 (m, 6H), 1.24-1.27 (m, 3H), 1.37 (s, 3H), 1.40-1.50 (m, 2H), 1.60-1.65 (m, 1H), 1.72 (s, 1H), 1.83 (d, J=14.88 Hz, 1H), 1.89 (s, 1H), 1.99-2.01 (m, 1H), 2.16-2.20 (m, 1H), 2.28-2.32 (m, 1H), 2.99-3.05 (m, 2H), 3.26-3.27 (m, 1H), 4.05-4.07 (m, 1H), 4.17 (s, 1H), 4.29 (d, J=14.88 Hz, 1H), 4.98-5.09 (m, 3H), 5.45 (d, J=8.28 Hz, 1H), 6.89 (s, 1H), 7.17-7.36 (m, 10H). ESI-MS m/z: 577.34 (M+H)$^+$.

Example 3: (R)-1-((2S,3R)-3-((benzyloxycarbonyl) amino)-2-hydroxy-4-phenylbu tyramide)-3-methyl-butyl Boric acid (4)

Compound 3 (2.88 g, 5.0 mmol) was dissolved in 50 mL of a 1:1 mixed solvent of anhydrous methanol and n-hexane, and isobutylboronic acid (1.27 g, 12.5 mmol) was added to it. 1 mol/L hydrochloric acid solution was added under ice bath conditions and continued stirring for 6 hours at room temperature. After standing for liquid separation, 2 mol/L sodium hydroxide was added to the lower layer to dissolve it, and extracted with dichloromethane three times. The aqueous phase was adjusted to pH=5 with 1N hydrochloric acid, extracted with DCM three times, combined the DCM phases, washed with saturated brine, dried over anhydrous magnesium sulfate, and evaporated to dryness to obtain a white solid 4 (0.77 g, 35%).

Example 4: (R)-1-((2S,3R)-3-amino-2-hydroxy-4-phenylbutyramide)-3-methylbu tylboronic acid (5)

Compound 4 (1.10 g, 2.5 mmol) was dissolved in 50 mL of anhydrous methanol, 10% palladium carbon 0.1 g was added, reacted at room temperature under hydrogen for 6 h, filtered and evaporated the solvent to obtain white solid 5 (1.26 g, 42%).

Example 5: 2,2'-(2-((R)-1-((2S,3R)-3-amino-2-hydroxy-4-phenylbutyramide)-3-methylbutyl)-5-oxo-1,3,2-dioxaborolan-4,4-diyl) diacetic acid (6)

Compound 5 (0.62 g, 2.0 mmol) was dissolved in 20 mL of ethyl acetate, and citric acid (0.38 g, 2.0 mmol) was added at 65° C. under oil bath. After reacting for 0.5 h, it was cooled to room temperature and continued stirring for 2 h. The solvent was evaporated to obtain the crude product, which was recrystallized from ethyl acetate to obtain white solid 6 (0.36 g, 40%). $^1$H-NMR (400 MHz DMSO-$d_6$): 0.77-0.87 (m, 6H), 1.18-1.30 (m, 2H), 1.65-1.75 (m, 1H), 2.20-2.36 (m, 1H), 2.56-2.84 (m, 4H), 2.96-3.06 (m, 1H), 3.18 (s, 1H), 3.49-3.71 (m, 1H), 3.86-3.96 (m, 1H), 7.22-7.36 (m, 5H), 7.60-7.97 (m, 3H), 11.93 (s, 2H). ESI-MS m/z: 465.20 (M+H)$^+$; that is the target compound 6 (Bestazomib Cirtate).

Example 6: Activity Test of Inhibition of Aminopeptidase N of Target Compound In Vitro Aminopeptidase N interacts with its commercial substrate L-leucyl p-nitroaniline (purchased from Sigma) to produce p-nitroaniline that is absorbed at 405 nm, and the concentration of p-nitroaniline is positively correlated to the enzyme activity. Measure the absorbance at 405 nm, and calculate the inhibition rate based on the absorbance of the inhibitor group and the control group, and calculate the $IC_{50}$ value. The experimental results are shown in Table 1.

TABLE 1

In vitro inhibition test results of Bestazomib Citrate, Bestazomib and positive control Bestatin

| Compd | $IC_{50}$ (μM)[a] APN | $IC_{50}$ (μM)[a] 20S Proteasome |
|---|---|---|
| Bestazomib Citrate | 2.14 | 8.56 |
| Bestazomib | 3.87 | 10.18 |
| Bestatin | 4.86 | ND[b] |
| Ixazomib | 18.23 | 0.0063 |

[a] The value in the table is the average of three tests, and
[b] ND: not detected.

The above test results show that the compound Bestazomib Citrate exhibits better APN inhibitory activity than the positive control drug Bestatin. The results show that, after the replacement of the carboxyl group of Bestatin with boric acid, it could still maintain the inhibitory activity on APN, and it could be used as the lead compound to find a new and efficient aminopeptidase N inhibitor, which has a good development prospect.

Example 7: Inhibitory Activity of Target Compound Against 20S Proteasome In Vitro The 20S proteasome detection kit (Calbiochems, EMD Millipore Co., USA) was used for in vitro proteasome activity test (*Clinical Cancer Research*, 2011, 17:5311-5321). The proteasome interacts with its substrate to produce the fluorescent substance 7-amino-4-methylcoumarin (7-AMC), and the concentration of 7-AMC is positively correlated with the activity of the proteasome. Measure the fluorescence intensity at 380/460 nm to calculate the inhibition rate based on the absorbance of the inhibitor group and the control group, and calculate the $IC_{50}$ value. The experimental results are shown in Table 1.

The above experimental results showed that the compound Bestazomib Citrate also showed inhibitory activity on the proteasome, but its inhibitory activity was weaker than the positive control drug Ixazomib. It shows that the compound Bestazomib Citrate has dual target inhibitory activity.

Example 8: The Inhibitory Activity of the Target Compound on Cell Proliferation In Vitro The in vitro cell proliferation inhibitory activity test of the target compound adopts the MTT method. Human leukemia K562 cell line, human myeloma U266 cell line, human lung cancer A549 cell, human prostate cancer PC-3 cell line, human lymphoma U937 cell line, human liver cancer PLC/PRF/5 cell line, and human embryonic kidney cell HEK293, human normal hepatocyte HL7702 were taken, and all adopted routine culture. Logarithmic growth phase cells were used in the experiment. The cell suspensions of the above cells were taken and counted under an inverted microscope, and the medium was added to adjust the number of cells to $1\times10^5$/mL. A 96-well cell culture plate was taken for cell inoculation and drug experiment. The peripheral holes are not used (filled with sterile PBS). Blank control group, negative control group, positive control group and a drug experiment group were set up. The blank control group only added 150 L/Well of cell culture solution, the negative control group was inoculated with 100 L/well of cell suspension and 50 L/well of cell culture medium was added, the positive control group was inoculated with 100 L/well of cell suspension and 50 L/well of positive control drug solution was added, and the drug experiment group was inoculated with 100 L/Well of cell suspension and 50 L/well of the test compound solution was added, the positive control group and the drug experimental group are respectively set up with 5 different final drug concentrations: 0.01, 0.1, 1, 10, 100 mol-L$^{-1}$, 3 parallel re-wells for each drug concentration. After the drug was added, the 96-well cell culture plate was incubated at 37° C., 5% $CO_2$ and saturated humidity for 48 hours, and 10 μL of 0.5% MTT staining solution was added to each well. After incubating for 4 hours, centrifuge at 2500 rpm for 30 min, then discard the medium in the plate wells, add 100 μL of DMSO to each well, and shake on a plate shaker for 15 min to dissolve the formazan crystals completely. Measure the OD value of each well with a microplate reader at a wavelength of 570 nm, and the cell growth inhibition rate is calculated according to the following formula:

$$\text{Inhibition rate}(\%) = \frac{\text{The average OD value of control well} - \text{The average OD value of experimental well}}{\text{The average OD value of control well}} \times 100\%$$

TABLE 2

Results of the inhibitory activity of Bestazomib Citrate and the positive control Bestatin on tumor cell proliferation ($IC_{50}$, μM[a])

| Cell lines | Bestazomib Citrate | Bestazomib | Bestatin |
|---|---|---|---|
| K562 | 12.28 ± 1.46 | 37.15 ± 2.28 | >200 |
| U266 | 21.72 ± 1.87 | 36.55 ± 2.07 | >200 |

TABLE 2-continued

Results of the inhibitory activity of Bestazomib Citrate and the
positive control Bestatin on tumor cell proliferation (IC$_{50}$, μM$^a$)

| Cell lines | Bestazomib Citrate | Bestazomib | Bestatin |
|---|---|---|---|
| A549 | 63.58 ± 5.71 | 98.36 ± 7.51 | >200 |
| PC-3 | 45.57 ± 3.16 | 65.74 ± 5.83 | >200 |
| U937 | 6.42 ± 0.64 | 15.49 ± 1.41 | >200 |
| PLC/PRF/5 | 54.70 ± 4.12 | 79.64 ± 6.32 | >200 |

$^a$The value in the table is the average of three tests

The test data in the above table shows that the compound Bestazomib Citrate has a certain proliferation inhibitory effect on the above-mentioned tumor cells. Compared with the positive control drug Bestatin, Bestazomib Citrate could significantly enhance the proliferation inhibition activity of human lymphoma cell U937, human leukemia cell K562 and human myeloma cell U266, and have obvious proliferation inhibitory activity on human lung cancer cell PC-3, human lung cancer cell A549 and human liver cancer cell PLC/PRF/5, having good development prospect (Table 2). In addition, research on the proliferation inhibitory activity of Bestazomib Citrate on human normal cells shows that, compared with the positive control drug Ixazomib, the inhibitory activity of Bestazomib Citrate on normal cells is much lower than that of Ixazomib, indicating that Bestazomib Citrate is safer and has a wider therapeutic window (Table 3).

TABLE 3

Results of the proliferation inhibitory activity of Bestazomib Citrate
and positive control Ixazomib on normal human cells (IC$_{50}$, μM$^a$)

| Cell lines | Bestazomib Citrate | Ixazomib |
|---|---|---|
| HEK293 | 445.95 ± 19.45 | 17.10 ± 2.27 |
| HL7702 | 370.70 ± 70.85 | 4.04 ± 0.63 |

$^a$The value in the table is the average of three tests

Example 9: Inhibition of Liver Cancer H22 Lung Metastasis by Target Compound 1. Establishment of Transplanted Tumor Model in Mice Take well-grown H22 mice with liver cancer, extract ascites, add sterile PBS solution to dilute to a concentration of 2.5×10$^7$/mL, and inoculate Kunming mice through tail vein with 200 μL each. The Kunming mice with overweight or underweight were excluded, randomly grouped, and the drug was administrated according to the dosing schedule.

2. Pharmacodynamic Test

The Kunming mice inoculated with H22 tumors were weighed and randomly divided into the following 6 groups, with 7 mice in each group. (1) Negative control: PBS; (2) Ixazomib high-dose group: 4 mg/kg/4d; (3) Ixazomib low-dose group: 2 mg/kg/4d; (4) Bestazomib Citrate Low-dose group: 2.69 mg/kg/4d; (5) Bestazomib Citrate medium-dose group: 3.59 mg/kg/4d; (4) Bestazomib Citrate high-dose group: 4.48 mg/kg/d. Beatazomib Citrate is administered once a day, every 5 days of administration, stop for 2 days, 7 days as a cycle, a total of two cycles (dosing volume: 200 μL/20 g each time per mouse, administration method: intragastric administration), the positive control Ixazomib was administered once every four days, and the weight of the mice was weighed with an electronic balance at the beginning and end of each cycle, and the average value was calculated. The mice were sacrificed 13 days after the inoculation. The calculation formula for the inhibition rate of lung metastasis of liver cancer was as follows:

$$\text{Inhibition rate}(\%) = \frac{\text{Number of lung metastases in the blank group} - \text{Number of lung metastases in the treatment group}}{\text{Number of lung metastases in the blank group}} \times 100\%$$

3. Result

Figure 2:
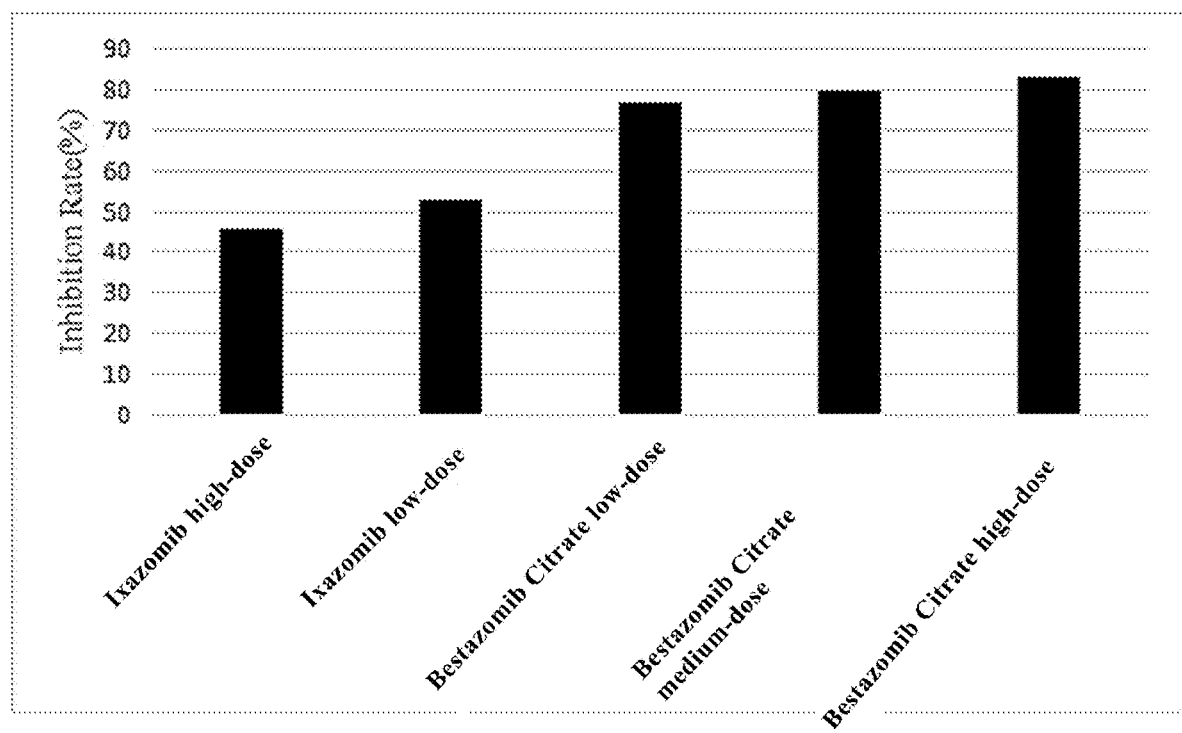
FIG. 2 shows the test results of the inhibition rate of inhibiting liver cancer H22 metastasis to the lung.
Figure 3:
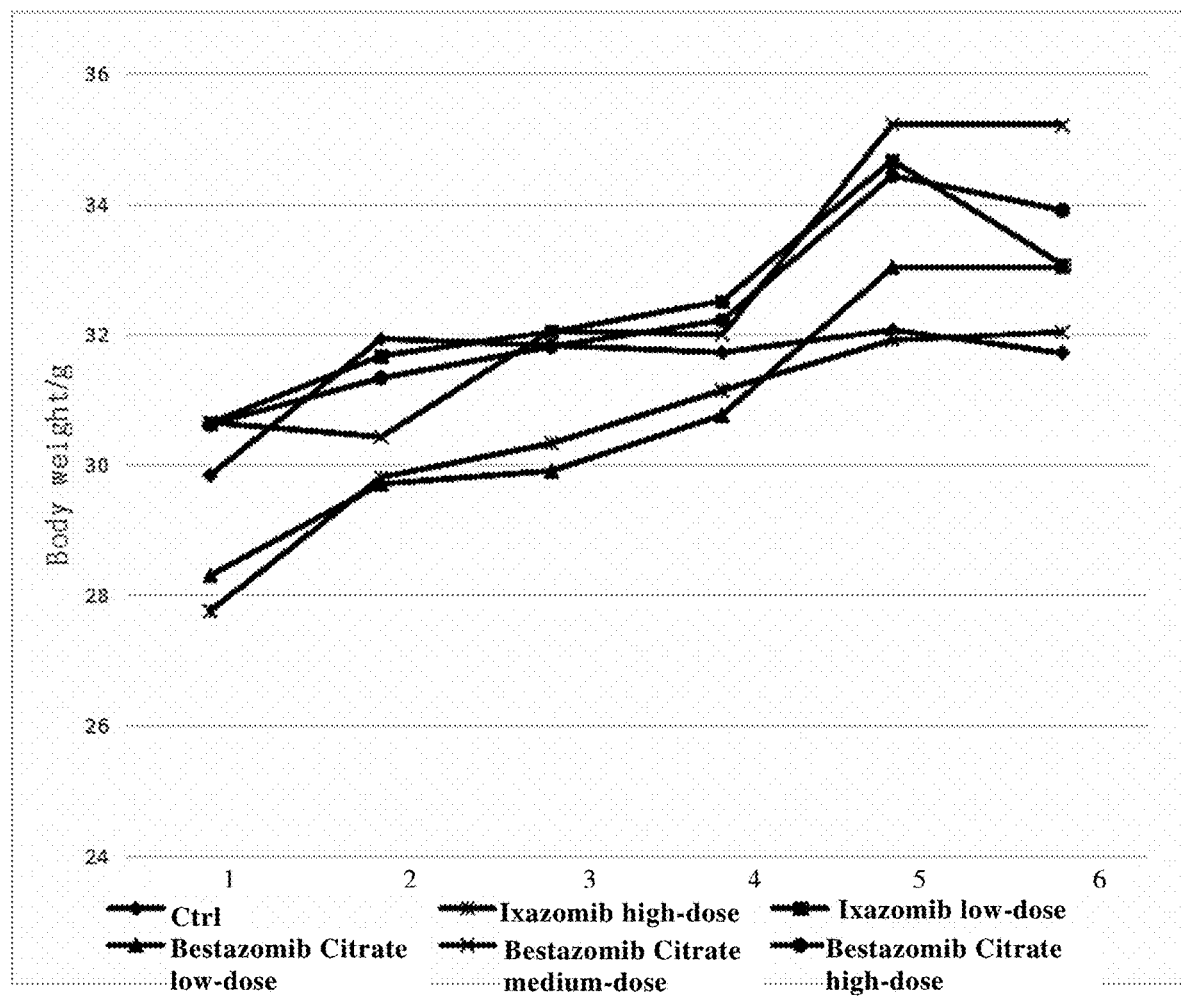
FIG. 3 shows the body weight change curve of each group of animals.
Figure 4:
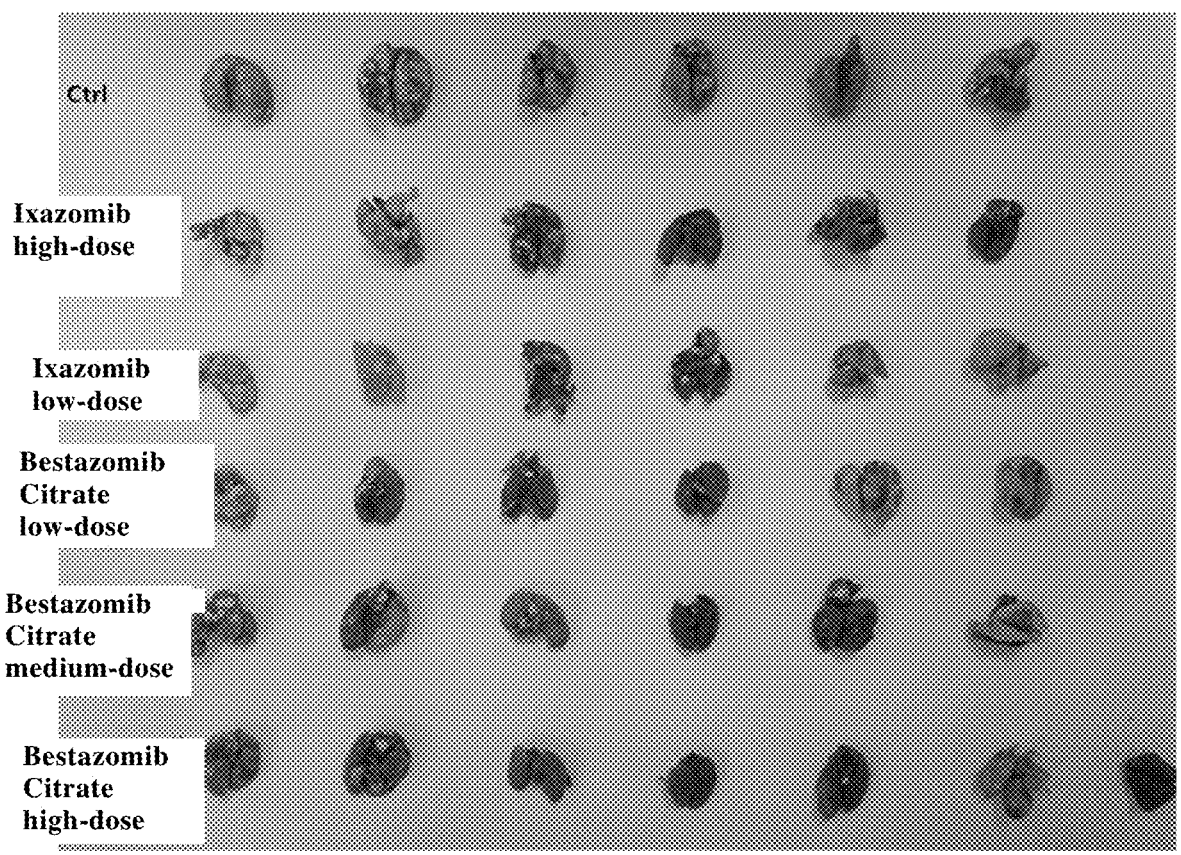
FIG. 4 shows the photos of lung organs and lung nodules in each group.

The number of lung nodules in each group was shown in FIG. 1, the test results of the inhibition rate of inhibiting liver cancer H22 metastasis to the lung were shown in FIG. 2, the body weight change curves of each group were shown in FIG. 3, and the photos of lung organs and lung nodules in each group were shown in FIG. 4.

The above test results showed that Bestazomib Citrate, as a multifunctional immune small molecule anticancer drug, has strong anti-tumor activity in vivo and in vitro, and has certain development and application prospects.

Example 10: Function Test of Clearance Rate of Charcoal Particles

1. Experimental Principle

The mononuclear macrophage system is a very important defense system, which has a powerful ability to swallow and clear foreign particles. When a certain concentration of charcoal particles enters the body through the tail vein of the mice, they are carried to the liver, spleen, etc. by the flow of blood, and the macrophages of these organs can remove these charcoal particles. Within a certain concentration range, the rate of macrophages' elimination of charcoal particles is exponentially related to their dose, that is, the rate of phagocytosis is directly proportional to the concentration of charcoal particles in the blood. Therefore, taking the logarithm of the concentration of charcoal particles in the blood of mice as the ordinate and the time as the abscissa, the slope K represents the phagocytic rate of macrophages, but this is an uncorrected phagocytic index. In fact, its phagocytic activity is also related to the weight of the liver and spleen of mice. Different weights result in different K values. Therefore, it is generally expressed by the corrected phagocytic index α, which reflects the phagocytic activity per unit tissue weight. The calculation formulas of K and a are as follows:

$$K = (\log A_1 - \log A_2)/(t_2 - t_1)$$

$$\alpha = (k^{1/3} \times \text{body weight})/(\text{liver weight} + \text{spleen weight})$$

2. Experimental Materials and Methods

Materials: Kunming mice (female, 4-5 weeks old), Indian ink, normal saline, Na$_2$CO$_3$ solution (0.1% g/v), UV ultraviolet visible photometer.

Kunming mice were randomly divided into groups and administered for 2 weeks. One hour after the last administration, each mouse was injected intravenously with 0.1 mL/10 g of Indian ink 5 times diluted with normal saline, and started timing immediately after injection, 20 μL of blood samples were accurately collected from the orbital venous plexus and added into 2 mL of 0.1% Na$_2$CO$_3$ solution at 2 min (t$_1$) and 10 min (t$_2$) time points, respectively. After mixing evenly, use 0.1% Na$_2$CO$_3$ solution as the control group, each administration group was the experimental group, the absorbance at two time points of t$_1$ and t$_2$ were measured by ultraviolet spectrophotometer at 600 nm, and counted as $A_1$ and $A_2$. The clearance index is calculated by the calculation formula of the above K value. In addition, after the completion of blood collection, the mice were sacrificed by neck removal, and the liver and spleen were taken out and weighed. Calculate the phagocytic index α.

TABLE 4

Macrophage charcoal particles clearance index (K) and phagocytic index (α) of Bestazomib Cirtate and positive control Ixazomib in mice

| Groups | Dosage (mg/kg/4 d) | carbon clearance index (K) [a] | phagocytosis index(α) [a] |
|---|---|---|---|
| Ctrl | 0 | 0.057 ± 0.0061 | 19.126 ± 0.685 |
| Ixazomib high-dose (po.) | 4 | 0.045 ± 0.0092 | 15.423 ± 1.053 |
| Ixazomib low-dose (po.) | 2 | 0.061 ± 0.0066 | 19.949 ± 0.718 |
| Bestazomib Citrate Low-dose (po.) | 2.69 | 0.066 ± 0.0077 | 24.842 ± 0.969 |
| Bestazomib Citrate Medium-dose (po.) | 3.59 | 0.076 ± 0.0016 | 21.620 ± 0.154 |
| Bestazomib Citrate High-dose (po.) | 4.48 | 0.063 ± 0.0002 | 21.628 ± 0.026 |

[a] The results presented were expressed as mean ± standard deviation.

The above test results showed that the phagocytic ability of macrophages in mice administrated Bestazomib Citrate was significantly stronger than that of the positive control Ixazomib, and had a certain dose-dependence. This result showed that Bestazomib Citrate could enhance the phagocytic ability of macrophages in mice, thereby enhancing the immune function of mice. Therefore, Bestazomib Citrate as a multifunctional immune small molecule anticancer drug has good development and application prospects.

Example 11: Survival Test of H22 Liver Ascites Model in Kunming Mice

Take well-grown H22 mice with liver cancer, extract ascites, add sterile PBS solution to dilute to a concentration of $2.5 \times 10^7$/mL, and inoculate the abdominal cavity of Kunming mice with 200 μL each. 5 days later, the animals were randomly grouped to administrate the drug. The day of inoculation was the first day. The body weight of the animals was recorded at the time of administration. The mice were randomly weighed and divided into the following 6 groups, with 10 mice in each group. (1) Negative control: PBS; (2) Ixazomib high-dose group: 4 mg/kg/4d; (3) Ixazomib low-dose group: 2 mg/kg/4d; (4) Bestazomib Citrate Low-dose group: 2.69 mg/kg/4d; (5) Bestazomib Citrate medium-dose group: 3.59 mg/kg/4d; (6) Bestazomib Citrate high-dose group: 4.48 mg/kg/d. The mice were administered according to the predetermined dosage, weighed and recorded respectively.

Use Origin7.5 software's one-way analysis of variance (One-Way ANOVA) function to calculate the overall difference; use t-test to compare each group with the blank group, and the life extension rate of each drug group was calculated by the following formula:

$$\text{Life extension rate(\%)} = \frac{\text{Average survival time of dosing group} - \text{Average survival time of } Ctrl \text{ group}}{\text{Average survival time of } Ctrl \text{ group}} \times 100\%$$

Figure 5:
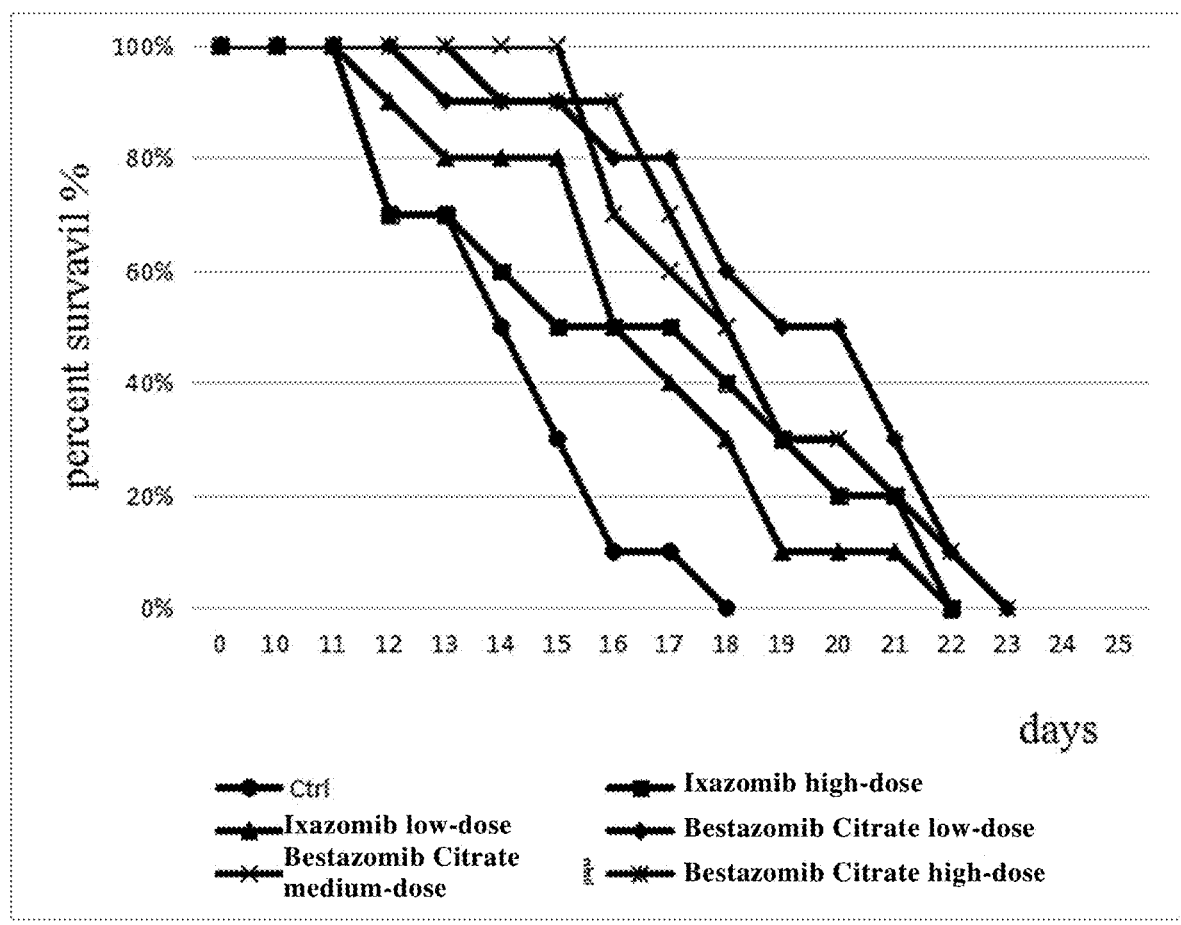
FIG. 5 shows the survival curve of animals in each group.
Figure 6:
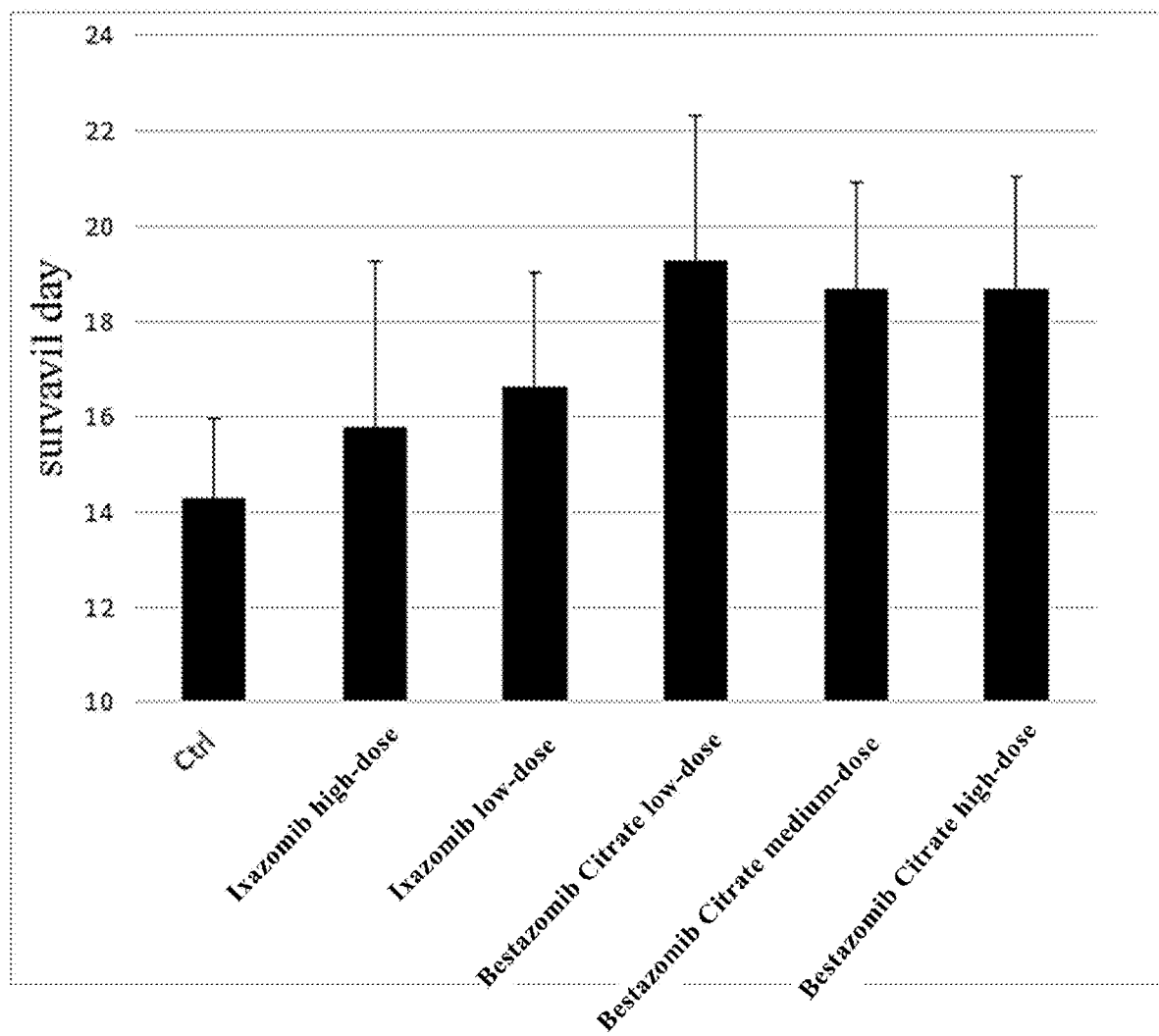
FIG. 6 shows the comparison of the survival days of animals in each group.

The survival curves of each group were shown in FIG. 5, and the comparison of survival days of animals in each group was shown in FIG. 6. The above test results showed that the survival time of mice administrated Bestazomib Citrate was better than the prolonged time of the positive drug Ixazomib under the premise of equal molar amount with the positive drug Ixazomib. Bestazomib Citrate as a multifunctional immune small molecule anticancer drug has good development and application prospects.

Example 12: Subcutaneous Tumor Survival Test of C57 Mice with B16F10 Melanoma Cells The B16F10 melanoma cells in the logarithmic growth phase were taken, diluted with sterile PBS solution to a concentration of $1.5 \times 10^7$ cells/mL, and inoculated them subcutaneously in C57 mice with 150 μL each. 5 days later, the animals were randomly assigned to administer the drug. The day of inoculation was the first day. The body weight of the animals was recorded at the time of administration. The mice were randomly weighed and divided into the following 5 groups. (1) negative control: PBS; (2) Ixazomib high-dose group: 4 mg/kg/4d; (3) Bestazomib Citrate low-dose group: 4 mg/kg/4d; (4) Bestazomib Citrate medium-dose group: 6 mg/kg/4d; (5) Bestazomib Citrate high-dose group: 9 mg/kg/4d. The mice were administered according to the predetermined dosage, weighed and recorded respectively. Continuous observation until the death of the mouse was the end of observation, and the time of death of each mouse was recorded. The time of death of the mice in each group was counted.

Use Origin7.5 software's one-way analysis of variance (One-Way ANOVA) function to calculate the overall difference; use t-test to compare each group with the blank group, and the life extension rate of each drug group was calculated by the following formula:

$$\text{Life extension rate(\%)} = \frac{\text{Average survival time of administration} - \text{Average survival time of } Ctrl \text{ group}}{\text{Average survival time of } Ctrl \text{ group}} \times 100\%$$

Figure 7:
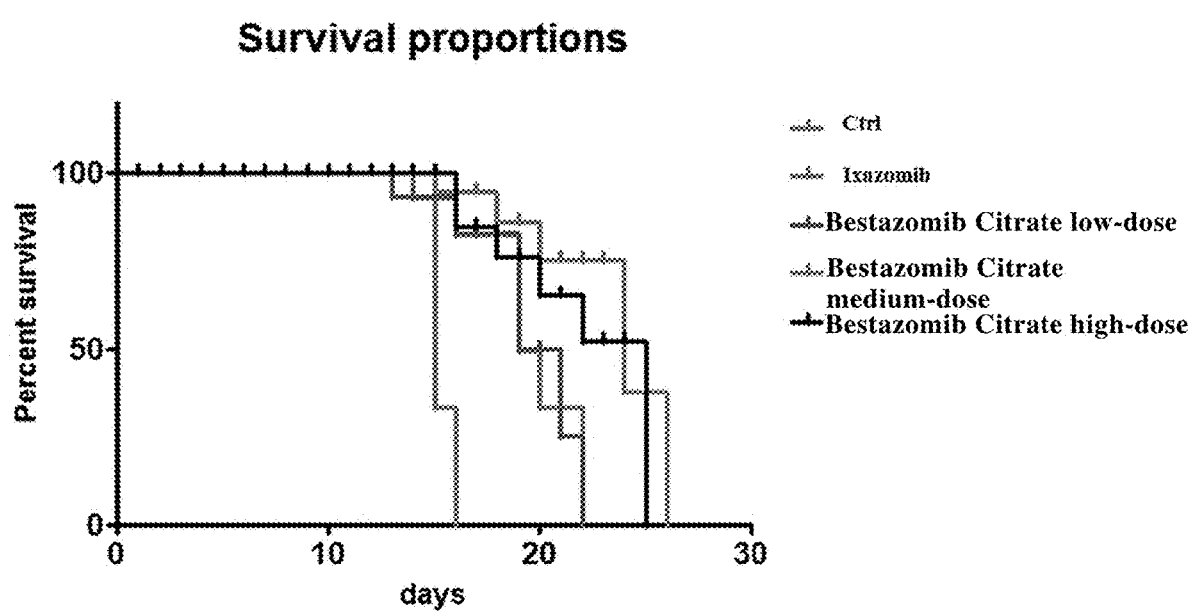
FIG. 7 shows the survival curve of each group.

The survival curves of each group were shown in FIG. 7. The above test results showed that Bestazomib Citrate could significantly prolong the survival time of B16F10 melanoma mice. Compared with the positive drug Ixazomib, Bestazomib Citrate has better survival time of mice in the medium-dose and high-dose than the positive drug Ixazomib. Bestazomib Citrate as a multifunctional immune small molecule anticancer drug has good development and application prospects.

The foregoing descriptions are only preferred examples of the application, and are not used to limit the application. For those skilled in the art, the application can have various modifications and changes. Any modification, equivalent replacement, improvement, etc. made within the spirit and principles of this application shall be included in the protection scope of this application.

The invention claimed is:

1. A compound represented by Formula I, or an optical isomer, a diastereomer, a racemate or a mixture of the three, or a pharmaceutically acceptable salt or a solvate thereof;

I

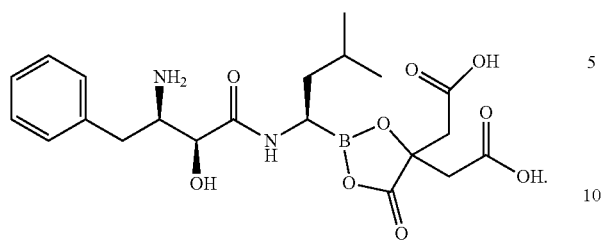

2. An intermediate compound represented by Formula II.

II

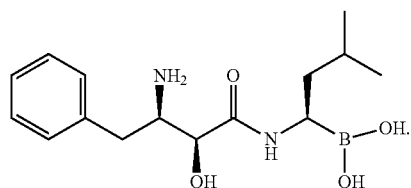

3. A method for preparing the compound of claim 1 comprising:

(Formula I)

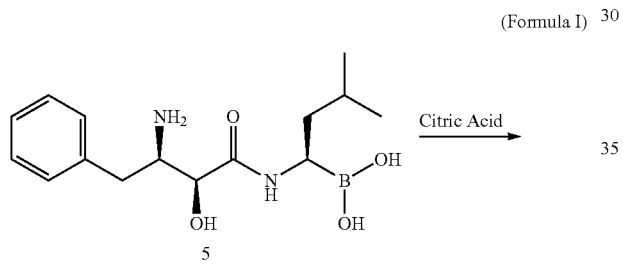

6, Bestazomib Citrate reacting intermediate 5 with citric acid to obtain the compound represented by Formula I.

4. A method for preparing the compound of claim 1, wherein the method comprises:
using (2S,3R)-3-amino-2-hydroxy-4-phenylbutyric acid as the raw material, the primary amino group is protected by Cbz protective group to obtain intermediate 2; reacting intermediate 2 with (R)-1-amino-3-methyl-butylboronic acid pinanediol ester trifluoroacetate in anhydrous DCM catalyzed by EDCI and HOBt to obtain intermediate 3; deprotecting the Cbz protective group of intermediate 3 by isobutylboronic acid to obtain intermediate 4; deprotecting Cbz of intermediate 4 under Pd/C and hydrogen to generate intermediate 5, and finally reacting intermediate 5 with citric acid to obtain the compound of Formula I, and wherein the intermediate 2 is 2

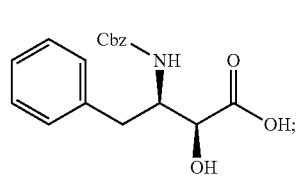

the intermediate 3 is

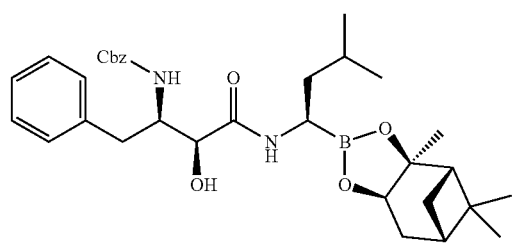

the intermediate 4 is

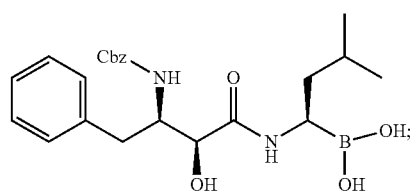

the intermediate 5 is

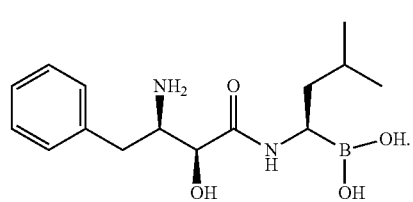

5. A method for inhibiting activity of both aminopeptidase N and proteasome, comprising contacting the compound according to claim 1, or an optical isomer, a diastereomer, a racemate or a mixture of the three, or a pharmaceutically acceptable salt thereof, or a solvate thereof with aminopeptidase N and proteasome.

6. A method for treating a tumor disease, comprising administering the compound according to claim 1, or an optical isomer, a diastereomer, a racemate or a mixture of the three, or a pharmaceutically acceptable salt thereof, or a solvate thereof to a subject in need thereof.

7. The method according to claim 6, wherein the tumor disease comprises: myeloma, leukemia or solid tumor.

8. A pharmaceutical composition, wherein an active ingredient of the pharmaceutical composition is the compound according to claim 1, or an optical isomer, a diastereomer, a racemate or a mixture of the three, or the pharmaceutically acceptable salt thereof, or the solvate thereof.

9. The pharmaceutical composition according to claim 8, wherein the pharmaceutical composition further comprises one or more pharmaceutically acceptable carriers or excipients.

10. The pharmaceutical composition according to claim 8, wherein the pharmaceutical composition is an oral preparation or an injection preparation.

11. A method for treating tumor diseases, comprising administering the pharmaceutical composition according to claim 8 to a subject in need thereof.

* * * * *